(12) United States Patent
Lutz

(10) Patent No.: US 7,342,044 B2
(45) Date of Patent: Mar. 11, 2008

(54) PRESERVATIVE BLENDS CONTAINING QUATERNARY AMMONIUM COMPOUNDS

(75) Inventor: Patrick Jay Lutz, Nazareth, PA (US)

(73) Assignee: Lonza Inc., Fair Lawn, NJ (US)

( * ) Notice: Subject to any disclaimer, the term of this patent is extended or adjusted under 35 U.S.C. 154(b) by 0 days.

(21) Appl. No.: 10/087,207

(22) Filed: Feb. 28, 2002

(65) Prior Publication Data

US 2002/0165283 A1    Nov. 7, 2002

Related U.S. Application Data

(60) Provisional application No. 60/345,878, filed on Oct. 19, 2001, provisional application No. 60/273,082, filed on Mar. 1, 2001.

(51) Int. Cl.
*A01N 43/16* (2006.01)
*A01N 37/10* (2006.01)
*A61K 31/35* (2006.01)

(52) U.S. Cl. .................. 514/460; 514/568; 514/570

(58) Field of Classification Search ............... 514/460, 514/568, 570
See application file for complete search history.

(56) References Cited

U.S. PATENT DOCUMENTS

| | | | | |
|---|---|---|---|---|
| 3,097,131 A | | 7/1963 | Ueno et al. ............. 167/31 |
| 3,236,730 A | * | 2/1966 | Miles et al. ............. 167/59 |
| 4,585,795 A | | 4/1986 | Linderborg ............. 514/558 |
| 4,844,891 A | | 7/1989 | Rosen et al. ............. 424/76 |
| 5,073,570 A | | 12/1991 | Tseng ................. 514/533 |
| 5,670,160 A | | 9/1997 | Eggensperger et al. ..... 424/405 |
| 5,885,593 A | | 3/1999 | Epstein ................ 424/401 |
| 6,150,403 A | * | 11/2000 | Biedermann et al. ....... 424/7 |

FOREIGN PATENT DOCUMENTS

| | | |
|---|---|---|
| DE | 2045337 | 4/1971 |
| DE | 3308303 | 9/1983 |
| DE | 4026756 | 2/1992 |
| EP | 0265202 | 10/1987 |
| EP | 0339121 | 4/1988 |
| EP | 0974359 | 7/1999 |
| GB | 1301316 | 12/1972 |
| JP | 4942901 | 9/1972 |
| JP | 5350245 | 5/1978 |
| JP | 56123906 | 9/1981 |
| JP | 57058625 | 4/1982 |
| JP | 57058624 | 8/1982 |
| JP | 5229904 | 9/1993 |
| JP | 94259415 | 9/1994 |
| JP | 6-313269 | 11/1994 |
| JP | 95141346 | 5/1995 |
| JP | 08092013 | 4/1996 |
| JP | 8310925 | 11/1996 |
| JP | 10087496 | * 4/1998 |
| JP | 999145 | 1/1999 |
| JP | 11279205 | * 10/1999 |
| JP | 2001139993 | 11/1999 |
| JP | 2000212090 | 8/2000 |
| JP | 99326614 | 5/2001 |
| WO | 94/27436 | 12/1994 |
| WO | 99/07331 | 2/1999 |
| WO | 99/37172 | 7/1999 |

OTHER PUBLICATIONS

Wan, Interaction of salicylic acid with quaternary ammonium compounds, 1968, J. of Pharmaceutical Sciences, vol. 57, No. 11, pp. 1903-1906.*
International Search Report; PCT/US02/06305; Feb. 28, 2002.

* cited by examiner

*Primary Examiner*—Alton Pryor
(74) *Attorney, Agent, or Firm*—Darby & Darby P.C.

(57) ABSTRACT

The present invention provides a biocidal composition comprising a synergistic mixture of certain quaternary ammonium biocides and one or more ketone acids, aromatic carboxylic acids, salts thereof, or mixtures thereof.

11 Claims, No Drawings

US 7,342,044 B2

PRESERVATIVE BLENDS CONTAINING QUATERNARY AMMONIUM COMPOUNDS

This application claims the benefit of U.S. Provisional Application No. 60/273,082, filed Mar. 1, 2001, and U.S. Provisional Application No. 60/345,878, filed Oct. 19, 2001, both of which are hereby incorporated by reference.

FIELD OF THE INVENTION

This invention relates to antimicrobial compositions containing (a) (i) a quaternary ammonium compound, (ii) a polymeric quaternary ammonium compound, or (iii) a mixture thereof and (b) (i) a cyclic or acyclic ketone acid or salt thereof, (ii) an aromatic carboxylic acid or a salt thereof, or (iii) a mixture thereof.

BACKGROUND OF THE INVENTION

Many quaternary ammonium compounds, such as benzethonium chloride, are known to be effective as antimicrobial agents and preservatives. However, benzethonium chloride and many other quaternary ammonium compounds are expensive. Furthermore, the efficacy of quaternary ammonium compounds generally are reduced when incorporated into anionic formulations. As a result, there is a continuing need for improved antimicrobial and preservative compositions which contain low concentrations of quaternary ammonium compounds and maintain their efficacy in anionic formulations.

SUMMARY OF THE INVENTION

Applicants have discovered that ketone acids, aromatic carboxylic acids, and salts thereof synergistically enhance the performance of certain quaternary ammonium biocides. The applicants have also discovered that while these quaternary ammonium biocides are frequently inactive in anionic formulations, mixtures containing at least one of these quaternary ammonium biocides and a ketone acid, an aromatic carboxylic acid, salt thereof, or a mixture thereof are active in anionic formulations.

The present invention provides a composition comprising (a)
  (i) a quaternary ammonium biocide having the formula $N^+R^1R^2R^3R^4X^-$ where $R^1$ and $R^2$ are independently unsubstituted or hydroxy substituted linear or branched $C_1$-$C_4$ alkyl, $-(CH_2CH_2O)_m CH_2CHCH_3OH$ where m is 1 to 10; $R^3$ is a substituted or unsubstituted benzyl, ethylbenzyl, methylnapthyl, or linear or branched $C_1$-$C_{22}$ alkyl; $R^4$ is $-R^5(O)_n(C_6H_4)R^6$ where n is 1; $R^5$ is a substituted or unsubstituted $C_1$-$C_8$ alkyl or $C_1$-$C_8$ alkoxyalkyl; $R^6$ is hydrogen or a substituted or unsubstituted, linear or branched $C_1$-$C_{12}$ alkyl; and $X^-$ is an anion, such as chloride, acetate, borate, propionate, carbonate, bicarbonate, or hydroxide,
  (ii) a polymeric quaternary ammonium biocide, or
  (iii) a mixture thereof; and
(b)
  (i) a ketone acid or salt thereof
  (ii) an aromatic carboxylic acid or a salt thereof, or
  (iii) a mixture thereof.

Preferably, the ketone acid is a cyclic ketone acid. The aforementioned mixtures are synergistic.

Another embodiment of the present invention is a method for inhibiting the growth of microorganisms on a substrate by applying an antimicrobial or preserving effective amount of the composition of the present invention.

DETAILED DESCRIPTION OF THE INVENTION

Unless otherwise specified, the term "substituted" as used herein includes, but is not limited to, at least one of the following substituents: $C_1$-$C_{12}$ alkyl (such as a $C_1$-$C_4$ alkyl), halogen (such as chlorine), nitro, and hydroxy.

The term "biocide" includes, but is not limited to, bactericides, fungicides, pesticides and agents which inhibit the growth of and/or destroy microorganisms and insects.

The term "anionic formulation" as used herein refers to formulations containing one or more anionic compounds, such as anionic surfactants.

The ketone acid or aromatic carboxylic acid enhances the biocidal efficacy of the quaternary ammonium biocide. These compositions are useful as antimicrobial, fungicidal, and bactericidal agents and as preservatives in the papermaking, textile, agricultural, and coating industries and in personal care, household, industrial, and institutional products. The composition may be incorporated into substrates susceptible to microbial growth as a preservative system. For example, the preservative system may be incorporated into or be a personal care product, such as a shampoo, conditioner, cream, lotion, cosmetic, or soap; a household product, such as a fabric softener, laundry detergent, or hard surface cleaner; or an industrial product, such as paint, wood, textile, adhesive, sealant, leather, rope, paper pulp, plastic, fuel, oil, rubber working fluid, metal working fluid, starch, or mineral slurry, such as a slurry of clay, calcium carbonate, or titanium oxide ($TiO_3$).

The applicants have also discovered that while the quaternary ammonium biocides, such as benzethonium chloride, frequently are inactive in anionic formulations, they are active in such formulations in the presence of ketone acids, aromatic carboxylic acids, and salts thereof.

Generally, the preservative system of the present invention acts quickly (e.g., reduces the bacteria count by 95, 99, 99.9, or 99.99% typically within an hour) and maintains efficacy (e.g., maintains less than 10 cfu/g) over long periods of time (e.g., for at least 28 days).

Quaternary Ammonium Biocides

According to one preferred embodiment, $R^5$ is $-CH_2CH_2OCH_2CH_2-$. More preferably, $R^4$ is [2-[2-(4-diisobutylphenoxy)ethoxy]ethyl]. According to another preferred embodiment, $R^4$ is benzyl.

Preferred quaternary ammonium biocides include, but are not limited to, salts of benzethonium ([2-[2-(4-diisobutylphenoxy)ethoxy]ethyl]dimethylbenzyl ammonium) (also referred to as benzethonium salts), such as benzethonium chloride (available as Hyamine 1622® from Lonza Inc. of Fair Lawn, N.J.); and salts of benzalkonium (benzyl alkyl dimethyl ammonium), such as benzalkonium chloride (available as Barquat® MB-50 and Barquat® MB-80 from Lonza Inc. of Fair Lawn, N.J.). Preferred benzalkonium salts include, but are not limited to, ($C_{12}$-$C_{18}$) alkyl benzyl dimethyl ammonium salts, such as ($C_{12}$-$C_{18}$) alkyl benzyl dimethyl ammonium chloride.

According to yet another preferred embodiment, the anion $X^-$ is carbonate.

The quaternary ammonium biocide may optionally be encapsulated by any method known in the art in order to increase its solubility in a desired solvent or formulation. For example, the quaternary ammonium biocide may be encapsulated in cyclodextrin; calixarenes, such as 4-tert-butylcali[4]arene; liposomes; catezones; or amphiphilic betaine polymers.

Polymeric Quaternary Ammonium Biocides

Suitable polymeric quaternary ammonium biocides include, but are not limited to, polymeric quaternary ammonium borates, such as those described in U.S. Pat. Nos. 4,970,201 and 5,304,237 (which is hereby incorporated by reference) and poly[oxyethylene(dimethylimino)-ethylene (dimethylimino) (available as Buckman WSCP from Buckman Laboratories of Memphis, Tenn.).

Ketone Acids

The ketone acid may be a cyclic or acyclic ketone acid. The term "cyclic ketone acid" as used herein includes compounds that have a ring containing a carbonyl group.

Suitable cyclic ketone acids include, but are not limited to, those having the formula

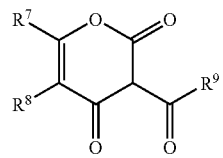

and salts thereof, wherein $R^7$, $R^8$, and $R^9$ are independently $C_1$-$C_{10}$ alkyl, $C_1$-$C_{10}$ alkenyl, $C_1$-$C_{10}$ alkenyl, aryl, aryl substituted with halogen, or ($C_1$-$C_{10}$ alkyl)aryl. Preferably, $R^7$, $R^8$, and $R^9$ are independently $C_1$-$C_4$ alkyl; or $R^7$ and $R^8$ form a 5-12 member ring. Preferred cyclic ketone acids, include, but are not limited to, those having the formula

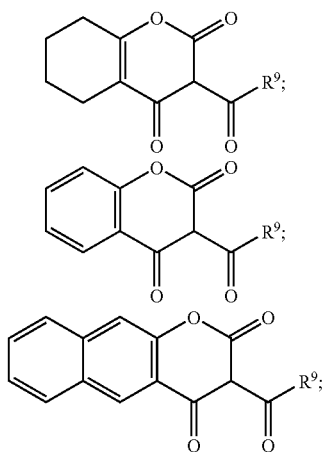

and salts thereof. A more preferred cyclic ketone acid is dehydroacetic acid and salts thereof (including hydrates thereof), such as sodium dehydroacetate (e.g., sodium dehydroacetate hydrate and sodium dehydroacetate monohydrate).

The cyclic ketone acid may optionally be encapsulated by any method known in the art to increase its solubility in a desired solvent or formulation. For example, the cyclic ketone acid may be encapsulated in cyclodextrin; calixarenes, such as 4-tert-butylcali[4]arene; liposomes; catezones; or amphiphilic betaine polymers. The cyclic ketone acid may be encapsulated by any method known in the art.

A preferred combination of cyclic ketone acid and quaternary ammonium biocide is dehydroacetic acid or a salt thereof and benzethonium chloride. A more preferred combination is sodium dehydroacetate and benzethonium chloride.

Aromatic Carboxylic Acids

Suitable aromatic carboxylic acids include, but are not limited to, benzoic acids, derivatives thereof, and salts thereof. According to one embodiment, the aromatic carboxylic acid has the formula

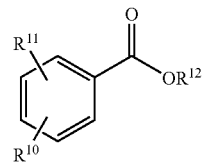

where $R^{10}$ and $R^{11}$ are independently H, —OH, or —OC(O)CH$_3$; and $R^{12}$ is H, Na, K, Ca, or Mg. When $R^{12}$ is Ca or Mg, the ratio of the aromatic carboxylic acid to Ca or Mg may be 1:1 or 2:1.

For example, the aromatic carboxylic acid can be a hydroxy benzoic acid, derivative thereof, or salt thereof. A preferred hydroxy benzoic acid is salicylic acid and salts thereof. Suitable salts of salicylic acid include, but are not limited to, sodium salicylate.

A preferred combination of aromatic carboxylic acid or salt thereof and quaternary ammonium biocide is sodium salicylate and benzethonium chloride.

The composition may include a solvent, such as water and water miscible solvents, including, but not limited to, alcohols, glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and an alcohol, such as phenoxyethanol and/or benzyl alcohol.

Other adjuvants may be included in the composition as known to one of ordinary skill in the art. Suitable adjuvants include, but are not limited to, preservatives; solubilizing agents; chelating agents, such as ethylenediaminetetraacetic acid (EDTA) and salts thereof and zeolites; surfactants, such as cationic, anionic, nonionic, and amphoteric surfactants; antioxidants, such as butylated hydroxyanisole (BHA) and butylhydroxytoluene (BHT); amine oxides; tertiary amines; zinc compounds; hydrotropes; flouride compounds; magnesium salts; calcium salts; carboxylic acids; phosphates; phosphonates; formaldehyde donors; glycereth-7; myristyl myristate; glutaraldehydes; biguanides; natural products, such as geranoil, usnic acid, and tea tree oils; and any combination of any of the foregoing.

Suitable preservatives include, but are not limited to, quaternary ammonium chlorides; quaternary ammonium carbonates; benzalkonium chloride; iodine containing compounds, such as 3-iodo-2-propynyl butyl carbamate (IPBC); hydantoins, such as dimethylhydantoin and halogenated hydantoins; isothiazolinones; parabens, such as methylparaben, ethylparaben, and propylparaben; chloroxylenol; chlorhexidine; phenoxyethanol; benzyl alcohol; phenethyl alcohol; benzoic acid and salts thereof; chlorobutanol; sorbic acid and salts thereof; triclosan; triclocarban; and any combination of any of the foregoing.

Typically, the composition is an aqueous or oil based system and is not an emulsion. In oil based systems, the quaternary ammonium biocide is preferably not encapsulated and the ketone acid is preferably not a hydrate. A suitable solvent for an oil based system is phenoxyethanol and/or benzyl alcohol.

The composition can be a liquid or a solid.

The weight ratio of (1) ketone acid, aromatic carboxylic acid, salts thereof, or mixtures thereof to (2) quaternary ammonium biocide, polymeric quaternary ammonium biocide, or mixtures thereof broadly ranges from about 0.00056:1 to about 1990:1 and preferably ranges from about 0.0056:1 to about 1400:1.

To prepare a formulation containing the composition of the present invention, a concentrate is generally first prepared. Table A illustrates the components and the ranges of components present in a typical concentrate (based upon 100% total weight of concentrate).

TABLE A

| Ranges | Quaternary Ammonium Biocide, Polymeric Quaternary Ammonium Biocide, or Mixtures Thereof | Ketone Acid, Aromatic Carboxylic Acid, Salts Thereof, or Mixtures Thereof |
|---|---|---|
| Broad | from about 0.05 to about 90% | from about 0.05 to about 99.5% |
| Preferred | from about 0.5 to about 40% | from about 0.50 to about 70% |
| More Preferred | from about 1 to about 20% | from about 5 to about 40% |

Before use, the concentrate is diluted, preferably with the same solvent as was used in the concentrate. Use dilutions of the composition typically comprise a biocidally, fungicidally, or bactericidally effective amount of (1) the quaternary ammonium biocide and/or polymeric quaternary ammonium biocide (i.e., component (a)) and/or (2) the mixture of components (a) and (b) (where component (b) is the ketone acid, aromatic carboxylic acid or salt thereof, or a mixture thereof). The use dilutions also typically comprise a biocidal, fungicidal, or bactericidal enhancing (or potentiating) effective amount of the ketone acid or salt thereof, aromatic carboxylic acid or salt thereof, or mixture thereof (i.e., component (b)). Generally, use dilutions contain from about 0.0001% or 0.01% to about 2% by weight of the concentrate. According to one preferred embodiment, use dilutions contain from about 0.1 to about 1% by weight of the concentrate. Table B illustrates the components and generally the ranges of components present in the use dilution (based upon 100% total weight of use dilution).

TABLE B

| Ranges | Quaternary Ammonium Biocide, Polymeric Quaternary Ammonium Biocide, or Mixtures Thereof | Ketone Acid, Aromatic Carboxylic Acid, Salts Thereof, or Mixtures Thereof |
|---|---|---|
| Broad | from about 0.00005 to about 0.45% | from about 0.00005 to about 0.5% |
| Preferred | from about 0.0005 to about 0.2% | from about 0.0005 to about 0.35% |
| More Preferred | from about 0.001 to about 0.1% | from about 0.005 to about 0.2% |

Yet another preferred embodiment is a preservative formulation comprising dehydroacetic acid, benzethonium chloride, salicylic acid and, optionally, benzoic acid, phenoxyethanol, and benzyl alcohol. The formulation in concentrated form may contain from about 5 to about 40% by weight of dehydroacetic acid, from about 1 to about 20% by weight of benzethonium chloride, from about 2.5 to about 20% by weight of salicylic acid, and, optionally, from about 2.5 to about 20% by weight of benzoic acid, from about 20 to about 50% by weight of phenoxyethanol, and from about 5 to about 50% by weight of benzyl alcohol, based upon 100% total weight of preservative formulation. A more preferred embodiment of the preservative formulation contains about 10% by weight of dehydroacetic acid, about 5% by weight of benzethonium chloride, and about 10% by weight of salicylic acid, and, optionally, about 10% by weight of benzoic acid, about 35% by weight of phenoxyethanol, and about 30% by weight of benzyl alcohol, based upon 100% total weight of preservative formulation.

Another embodiment of the present invention is a method for inhibiting the growth of microorganisms, bacteria (e.g., *S. aureus* (ATCC # 6538), *P. aeruginosa* (ATCC # 9027), and *E. coli* (ATCC # 8739)), and/or fungi (e.g., *Candida albicans* and *Aspergillus niger*) on a substrate by applying an antimicrobial, bactericidal, or fungicidal effective amount of the composition of the present invention to the substrate. The composition may be applied to the substrate by any method known in the art including, but not limited to, brushing, dipping, soaking, vacuum impregnation, and pressure treatment.

The composition of the present invention may be prepared by mixing the ketone acid or salt thereof, the aromatic carboxylic acid or salt thereof, quaternary ammonium biocide, polymeric quaternary ammonium biocide, solvents, and adjuvants. The mixture may be heated and/or stirred to expedite mixing.

DESCRIPTION OF THE PREFERRED
EMBODIMENTS

The following examples illustrate the invention without limitation. All parts and percentages are given by weight unless otherwise indicated.

EXAMPLE 1

Each anionic shampoo sample in Table 1 below was tested as follows. A standardized mixed bacterial solution was prepared according to the following procedure. 3 agar stabs of *S. aureus* (ATCC # 6538), *P. aeruginosa* (ATCC # 9027), and *E. coli* (ATCC # 8739) were separately incubated at about 35° C. for about 24 hours. Each stab was then washed with 3 mL of sterile 0.85% saline solution. The washes of the 3 stabs were pooled together to form an organism mixture. The absorbance of the organism mixture at 530 nm was adjusted to about 1.00 by adding saline. The spectrometer was calibrated with a saline blank. A 5 mL aliquot of the organism mixture was mixed together to produce the standardized mixed bacterial solution. Then, 40 g of each shampoo sample was inoculated with 0.2 mL of the standardized mixed bacterial solution and mixed. 1 g of the mixture was added to a sterile 20×150 mm screw cap test tube.

9 mL of sterile D/E neutralizer broth was added to the test tube and mixed to form a $10^{-1}$ dilution. Serial dilutions were prepared through to a $10^{-6}$ dilution with phosphate buffered water. The serial dilutions were plated onto Tryptic Soy Agar and incubated for 2 days at about 35° C. Bacteria counts were performed after 0 and 14 days. The results are shown in Table 1.

The anionic protein shampoo composition was comprised of 35% by weight of sodium lauryl ether sulfate; 25% by weight of triethanolamine lauryl sulfate; 3% by weight coconut diethanolamide (cocamide DEA); 1% by weight of hydrolyzed collagen, available as Polypro 5000™ from Hormel Foods of Austin, Minn.; and 36% by weight of deionized water.

The sodium dehydroacetate monohydrate, sodium salicylate, and Hyamine® 1622 shampoo samples were prepared by mixing the appropriate amounts of the preservatives and the aforementioned anionic protein shampoo composition and heating the mixture to about 50° C. for about 15 minutes.

TABLE 1

| Shampoo | S. aureus, P. aeruginosa, and E. coli (cfu/g) | |
|---|---|---|
| | Day 0 | Day 14 |
| Unpreserved Anionic Protein Shampoo Composition | 3.0 × 10⁶ | 3.0 × 10⁷ |
| 0.25% Sodium Dehydroacetate Monohydrate[1] and 0.50% Hyamine® 1622[2]* | 3.0 × 10⁶ | <10 |
| 0.5% Sodium Salicylate[3] and 0.5% Hyamine® 1622[2]* | 3.0 × 10⁶ | <10 |
| 0.5% Sodium Dehydroacetate Monohydrate[1]* | 3.0 × 10⁶ | 4.0 × 10³ |
| 1.0% Hyamine® 1622[2]* | 3.0 × 10⁶ | 8.5 × 10⁶ |
| 1.0% Sodium Salicylate[3]* | 3.0 × 10⁶ | 5.0 × 10² |

All percentages in Table 1 are in percent by weight based upon 100% by weight of total shampoo.
[1]Sodium dehydroacetate monohydrate is available from Lonza Inc. of Fair Lawn, NJ.
[2]Hyamine® 1622 is diisobutylphenoxyethoxyethyl dimethylbenzyl ammonium chloride (benzethonium chloride) and is available from Lonza Inc. of Fair Lawn, NJ.
[3]Sodium salicylate is available from Sigma Chemical Co. of St. Louis, MO.
*Below the specified concentrations of preservative, the shampoos contained ≧ 10 cfu/g after 14 days.

Synergism for the sodium dehydroacetate monohydrate/Hyamine® 1622 and sodium salicylate/Hyamine® 1622 solutions in Table 1 against *S. aureus*, *P. aeruginosa*, and *E. coli* was calculated by the method described in C. E. Kull et al., "Mixtures of Quaternary Ammonium Compounds and Long-chain Fatty Acids as Antifungal Agents", *Applied Microbiology*, 9:538-541 (1961). The synergism value ($Q_A/Q_a+Q_B/Q_b$) in Table 2 was determined. $Q_A$ is the concentration of sodium dehydroacetate monohydrate or sodium salicylate (in percent by weight) in the mixture, which yielded 100% retardation of the bacteria, i.e., resulted in a plate count of <10 cfu/g after 14 days. $Q_a$ is the concentration of sodium dehydroacetate monohydrate or sodium salicylate alone (in percent by weight) required to yield 100% retardation of the bacteria. $Q_B$ is the concentration of Hyamine® 1622 (in percent by weight) in the mixture, which yielded 100% retardation of the bacteria. $Q_b$ is the concentration of Hyamine® 1622 alone (in percent by weight) required to yield 100% retardation of the bacteria.

When the value of ($Q_A/Q_a+Q_B/Q_b$) is less than one, the mixture is synergistic. Values for ($Q_A/Q_a+Q_B/Q_b$) of 1 and greater than 1, represent an additive effect and an antagonistic effect, respectively.

The results are shown in Table 2 below.

TABLE 2

| Preservative Mixture | $Q_A$ | $Q_B$ | $Q_a$ | $Q_b$ | $Q_A/Q_a + Q_B/Q_b$ |
|---|---|---|---|---|---|
| 0.25% Sodium Dehydroacetate Monohydrate and 0.50% Hyamine® 1622 | 0.25% | 0.50% | >0.50% | >1.00% | <1 |
| 0.5% Sodium Salicylate and 0.5% Hyamine® 1622 | 0.5% | 0.5% | >1.00% | >1.00% | <1 |

EXAMPLE 2

The procedure described in Example 1 was repeated with the anionic shampoos in Table 3 below. The bacterial counts were performed after 0 and 7 days. The dehydroacetic acid (available from Lonza Inc. of Fair Lawn, N.J.) and Hyamine® 1622 shampoo samples were prepared by mixing the appropriate amounts of the preservatives and the anionic protein shampoo composition and heating the mixture to about 50° C. for about 15 minutes. The results are shown in Table 3 below.

TABLE 3

| Shampoo | S. aureus, P. aeruginosa, and E. Coli (cfu/g) | |
|---|---|---|
| | Day 0 | Day 7 |
| Unpreserved Anionic Protein Shampoo Composition | 3.0 × 10⁶ | 3.0 × 10⁷ |
| 0.1% Dehydroacetic Acid and 0.5% Hyamine® 1622 | 3.0 × 10⁶ | <10 |
| 0.2% Dehydroacetic Acid | 2.5 × 10⁶ | 4.4 × 10⁴ |
| 1.0% Hyamine® 1622 | 3.0 × 10⁶ | 3.0 × 10⁷ |

Synergism for the dehydroacetric acid/Hyamine® 1622 mixture in Table 3 against *S. aureus*, *P. aeruginosa*, and *E. coli* was determined by the procedure described in Example 1. The results are shown in Table 4 below.

TABLE 4

| Preservative Mixture | $Q_A$ | $Q_a$ | $Q_B$ | $Q_b$ | $Q_A/Q_a + Q_B/Q_b$ |
|---|---|---|---|---|---|
| 0.1% Dehydroacetic Acid and 0.5% Hyamine® 1622 | 0.1% | >0.2% | 0.5% | >1.0% | <1 |

EXAMPLE 3

The procedure described in Example 1 was repeated with the anionic shampoos in Table 5 below. The salicylic acid (available from Spectrum Chemical of New Brunswick, N.J.) and Hyamine® 1622 shampoo samples were prepared by mixing the appropriate amounts of the preservatives and the anionic protein shampoo composition and heating the mixture to about 50° C. for 15 minutes. The results are shown in Table 5 below.

TABLE 5

| Shampoo | S. aureus, P. aeruginosa, and E. Coli (cfu/g) | |
|---|---|---|
| | Day 0 | Day 14 |
| Unpreserved Anionic Protein Shampoo Composition | 3.0 × 10⁶ | 1.0 × 10⁷ |

TABLE 5-continued

| Shampoo | S. aureus, P. aeruginosa, and E. Coli (cfu/g) | |
| --- | --- | --- |
|  | Day 0 | Day 14 |
| 0.1% Salicylic Acid and 0.5% Hyamine ® 1622 | $3.0 \times 10^6$ | <10 |
| 1.0% Hyamine ® 1622 | $3.0 \times 10^6$ | $8.5 \times 10^6$ |
| 0.2% Salicylic Acid | $3.1 \times 10^6$ | $6.5 \times 10^6$ |

Synergism for the salicylic acid/Hyamine® 1622 solution in Table 5 against *S. aureus, P. aeruginosa*, and *E. coli* was determined by the procedure described in Example 1. The results are shown in Table 6 below.

TABLE 6

| Preservative Mixture | $Q_A$ | $Q_a$ | $Q_B$ | $Q_b$ | $Q_A/Q_a + Q_B/Q_b$ |
| --- | --- | --- | --- | --- | --- |
| 0.1% Salicylic Acid and 0.5% Hyamine ® | 0.1% | >0.2% | 0.5% | >1.0% | <1 |

EXAMPLE 4

A preservative formulation as described in Table 7 below was prepared by mixing the ingredients.

TABLE 7

| Ingredient | % (w/w) |
| --- | --- |
| Dehydroacetic Acid | 10 |
| Salicylic Acid | 10 |
| Benzoic Acid | 10 |
| Benzethonium Chloride | 1 |
| Phenoxyethanol | 37 |
| Benzyl Alcohol | 32 |

EXAMPLE 5

A preservative formulation as described in Table 8 below was prepared by mixing the ingredients.

TABLE 8

| Ingredient | % (w/w) |
| --- | --- |
| Dehydroacetic Acid | 10 |
| Salicylic Acid | 10 |
| Benzoic Acid | 10 |
| Benzethonium Chloride | 5 |
| Phenoxyethanol | 35 |
| Benzyl Alcohol | 30 |

EXAMPLE 6

Each anionic shampoo sample in Table 9 below was tested as follows. A standard mixed bacterial solution was prepared according to the following procedure. 2 agar slants of *Candida albicans* and 4 agar slants of *Aspergillus niger* were separately incubated at about 25° C. for about 48 hours and 7 days, respectively. Each slant was washed with 3 mL of sterile 0.85% saline solution, collected and macerated in a tissue grinder. Sufficient amounts of 0.85% saline solution were added to each slant to obtain a visual count under a microscope with a Neubauer Hemocytometer of each innoculum of *C. albicans* and *A. niger*. Equal volumes of each standardized innoculum of *C. albicans* and *A. niger* were mixed together to form the standardized mixed fungal solution.

40 g of each shampoo sample was inoculated with 0.4 mL of the standardized mixed fungal solution and mixed. 1 g of the mixture was added to a sterile 20×150 mm screw cap test tube.

9 mL of sterile D/E neutralizer broth was added to the test tube and mixed to form a $10^{-6}$ dilution. Serial dilutions were prepared through to a $10^{-10}$ dilution with phosphate buffered water. The serial dilutions were plated onto Sabourand dextrose agar and incubated 5 days at about 25° C. Fungal counts were performed after 0 and 14 days. The results are shown in Table 9.

The anionic protein shampoo composition is described in Example 1. The shampoo samples were prepared by mixing the appropriate amounts of the preservatives and the anionic protein shampoo composition and heating the mixture to about 50° C. for about 15 minutes.

TABLE 9

| Shampoo | Fungal Plate Count (cfu/g) | |
| --- | --- | --- |
|  | Day 0 | Day 14 |
| Unpreserved Anionic Protein Shampoo Composition | $1.6 \times 10^4$ | $1.5 \times 10^5$ |
| 1.0% Benzethonium Chloride | $2.4 \times 10^5$ | $2.0 \times 10^4$ |
| 0.6% Example 4 | $2.7 \times 10^5$ | $1.0 \times 10^3$ |
| 0.6% Example 5 | $1.1 \times 10^5$ | $7.0 \times 10^1$ |

The results in Table 9 show that benzethonium chloride is inactivated in anionic formulations. 1.0% or 10,000 ppm of benzethonium chloride is ineffective at reducing the mixed fungi in the anionic shampoo. Shampoo sample containing 0.6% of Example 4 (60 ppm of benzethonium chloride) exhibited a 2 log reduction in the fungal plate count. The shampoo sample containing 0.6% of Example 5 (300 ppm of benzethonium chloride) exhibited a 4 log reduction in the fungal plate count. This demonstrates that the preservative blend of the present invention potentiates the fungicidal efficacy of the benzethonium chloride in anionic formulations.

EXAMPLE 7

Each cream sample in Table 10 below was tested by the procedure described in Example 1. A glyceryl monostearate (GMS) cream as described in Table 10 below was prepared as follows. The polyoxyethylene glyceryl monostearate, glyceryl monostearate, cetearyl alcohol, and myristyl propionate were mixed and heated to 60° C. in a first container. The glycerin and sterile deionized water were mixed and heated to 60° C. in a second container. The solution in the first container was poured into the second container. The second container was maintained at 60° C. for 10 minutes. The solution in the second container was allowed to cool. The pH of the solution was adjusted to pH 7 with sodium hydroxide to yield the GMS cream.

TABLE 10

| Ingredient Trade Name | Chemical Name | Amount (% w/w) |
| --- | --- | --- |
| Aldosperse ® MS-20 (Lonza) | Polyoxyethylene (POE) glyceryl monostearate | 4.00 |
| Aldo ® (Lonza) | Glyceryl monostearate | 6.00 |
| TA 1618 (Proctor & Gamble) | Cetearyl alcohol | 1.50 |

TABLE 10-continued

| Ingredient Trade Name | Chemical Name | Amount (% w/w) |
|---|---|---|
| Lonzest ® 143-S (Lonza) | Myristyl propionate | 8.00 |
| Glycon ® G-100 (Lonza) | Glycerin | 5.00 |
| — | Sterile Deionized Water | 75.50 |
| Total | | 100.00 |

The 0.4% Example 5 sample was prepared by mixing the appropriate amounts of the preservatives and the GMS cream and heating the mixture to 50° C. for 10-15 minutes. The results are shown in Table 11 below.

TABLE 11

| Cream | S. aureus, P. aeruginosa, and E. coli (cfu/g) | | | |
|---|---|---|---|---|
| | 1 Hour | 3 Hours | 24 Hours | 28 Days |
| Unpreserved GMS Cream | $5.3 \times 10^6$ | $6.3 \times 10^6$ | $5.0 \times 10^6$ | $3.0 \times 10^6$ |
| 0.4% Example 5 | <10 | <10 | <10 | <10 |

While most preservatives have slow efficacy (e.g., require 3 or more days to reduce the number of microorganisms), the preservative system shown in Table 11 acts quickly (e.g., typically within an hour) and maintains efficacy over long periods of time (e.g., for at least 28 days).

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

The invention claimed is:

1. A preservative formulation comprising a synergistic mixture of:
   (a) dehydroacetic acid or a salt thereof;
   (b) a benzethonium salt;
   (c) salicylic acid or a salt thereof;
   (d) benzoic acid or a salt thereof;
   (e) phenoxyethanol; and
   (f) beuzyl alcohol.

2. The preservative formulation of claim 1 comprising:
   (a) from about 5 to about 40% by weight of dehydroacetic acid;
   (b) from about 1 to about 20% by weight of benzethonium chloride;
   (c) from about 2.5 to about 20% by weight of salicylic acid;
   (d) from about 2.5 to about 20% by weight of benzoic acid;
   (e) from about 20 to about 50% by weight of phenoxyethanol; and
   (f) from about 5 to about 50% by weight of benzyl alcohol, based upon 100% total weight of preservative formulation.

3. The preservative formulation of claim 2 comprising:
   (a) about 10% by weight of dehydroacetic acid;
   (b) about 5% by weight of benzethonium chloride;
   (c) about 10% by weight of salicylic acid;
   (d) about 10% by weight of benzoic acid;
   (e) about 35% by weight of phenoxyethanol; and
   (f) about 30% by weight of benzyl alcohol, based upon 100% total weight of preservative formulation.

4. A composition comprising from about 0.01 to about 2% by weight of the preservative composition of claim 2.

5. A personal care product comprising a preservative system, the preservative system comprising a synergistic mixture of:
   (a) a benzethonium salt; and
   (b) dehydroacetic acid or a salt thereof.

6. The personal care product of claim 5, wherein the personal care product is a shampoo, conditioner, cream, lotion, cosmetic, or soap.

7. The personal care product of claim 6, wherein the personal care product is a shampoo.

8. The personal care product of claim 6, wherein the personal care product is a conditioner.

9. The personal care product of claim 6, wherein the personal care product is a soap.

10. The personal care product of claim 5, comprising an anionic formulation.

11. The personal care product of claim 5, wherein the benzethonium salt is benzethonium chloride.

* * * * *